United States Patent
Lewis

(10) Patent No.: US 9,149,624 B2
(45) Date of Patent: Oct. 6, 2015

(54) DISINFECTING MALE LUER CONNECTOR CAPS

(75) Inventor: Stephen Lewis, San Diego, CA (US)

(73) Assignee: CareFusion 303, Inc., San Diego, CA (US)

(*) Notice: Subject to any disclaimer, the term of this patent is extended or adjusted under 35 U.S.C. 154(b) by 793 days.

(21) Appl. No.: 12/683,017

(22) Filed: Jan. 6, 2010

(65) Prior Publication Data
US 2011/0054440 A1    Mar. 3, 2011

Related U.S. Application Data

(60) Provisional application No. 61/239,385, filed on Sep. 2, 2009.

(51) Int. Cl.
*A61M 5/315*    (2006.01)
*A61M 39/16*    (2006.01)
*A61M 39/20*    (2006.01)

(52) U.S. Cl.
CPC .............. *A61M 39/16* (2013.01); *A61M 39/20* (2013.01); *A61M 39/162* (2013.01); *A61M 39/165* (2013.01); *A61M 2039/205* (2013.01)

(58) Field of Classification Search
CPC ... A61M 39/20; A61M 39/02; A61M 39/162; A61M 5/282; A61M 5/347
USPC ......... 604/236, 533–284, 500, 513, 192, 110, 604/197–200
See application file for complete search history.

(56) References Cited

U.S. PATENT DOCUMENTS

| | | | |
|---|---|---|---|
| 4,878,516 A | 11/1989 | Mathieu | |
| 5,190,534 A | 3/1993 | Kendell | |
| 5,195,957 A | 3/1993 | Tollini | |
| 5,334,188 A | 8/1994 | Inoue et al. | |
| 5,385,372 A * | 1/1995 | Utterberg | 285/332 |
| 6,152,913 A * | 11/2000 | Feith et al. | 604/533 |
| 7,184,825 B2 | 2/2007 | Leinsing | |
| 2007/0112333 A1* | 5/2007 | Hoang et al. | 604/533 |
| 2009/0008393 A1* | 1/2009 | Howlett et al. | 220/380 |

FOREIGN PATENT DOCUMENTS

| | | |
|---|---|---|
| DE | 2818146 | 11/1979 |
| EP | 1331020 | 7/2003 |

(Continued)

OTHER PUBLICATIONS

International Search report dated Mar. 1, 2011 from related PCT App. No. PCT/US2010/047359.

(Continued)

*Primary Examiner* — Phillip Gray
(74) *Attorney, Agent, or Firm* — McDermott Will & Emery LLP

(57) ABSTRACT

A system and method for disinfecting an exposed portion of a female luer connector is disclosed. A male luer connector coupled to a male luer connector cap is provided where the male luer connector cap has a chamber containing a disinfectant and a sealing member for sealing the disinfectant in the chamber. The chamber is at least partly opened and the disinfectant exposed by movement of the sealing member. An exposed surface of a female luer connector is caused to come in contact with the disinfecting fluid in the chamber prior to the female luer connector mating with the male luer connector.

22 Claims, 6 Drawing Sheets

(56) References Cited

FOREIGN PATENT DOCUMENTS

| JP | H06279062 | 10/1994 |
|---|---|---|
| JP | 2000515797 A | 11/2000 |
| JP | 2002291906 A | 10/2002 |
| JP | 2009500112 A | 1/2009 |
| RU | 2218950 C2 | 12/2003 |
| WO | WO-2007008511 A2 | 1/2007 |
| WO | WO-2008089196 A2 | 7/2008 |

OTHER PUBLICATIONS

Japanese Office Action in Japanese Patent Application No. 2012-527979 dated Jul. 25, 2014.
Chinese Office Action in Chinese Patent Application No. 201080038919.X dated Sep. 9, 2014, 12 pages including English translation.
Mexican Office Action in Mexican Patent Application No. MX/a/2012/002429 dated Oct. 30, 2014, 4 pages.
Russian Decision of Grant in Application No. 2012111264, dated Jan. 12, 2015, 11 pages.
Australian Examination Report No. 1 in Australian Application No. 2010289622, dated Feb. 2, 2015, 3 pages.
Communication pursuant to Article 94(3) EPC in European Application No. 10749587, dated Oct. 8, 2014, 4 pages.
First Chinese Office Action in Chinese Application No. 201080038919, dated Jun. 21, 2013, 13 pages.
Mexican Office Action No. 1 in Mexican Application No. MX/a/2012/002429, dated Jun. 17, 2014, 5 pages.
Japanese Decision to Grant in Japanese Application No. 2012-527979, dated Mar. 20, 2015, 3 pages.
Chinese Notice of Allowance in Chinese Application No. 201080038919.X, dated Apr. 8, 2015, 2 pages.
International Preliminary Report on Patentability for PCT Application No. PCT/US2010/047359 dated Apr. 21, 2012.
Conical fittings with a 6% (Luer) taper for syringes, needles and certain other medical equipment—Part 1: General Requirements, ISO 594/1-1986 (E).
Conical fittings with a 6% (Luer) taper for syringes, needles and certain other medical equipment—Part 2: Lock fittings, ISO 594-2: 1998 (E).

* cited by examiner

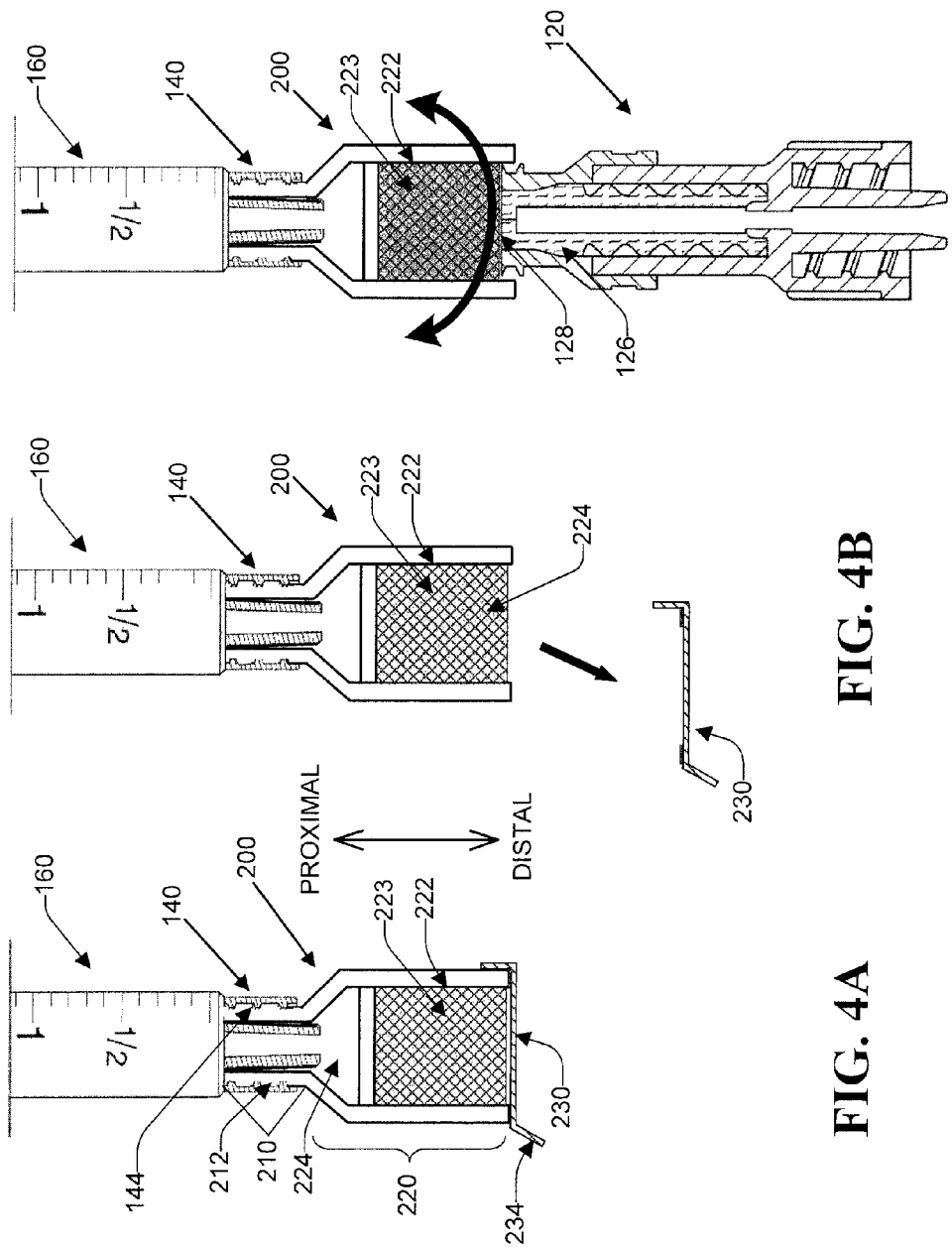

DISINFECTING MALE LUER CONNECTOR CAPS

STATEMENT OF RELATED APPLICATIONS

This application claims priority to U.S. Provisional Application No. 61/239,385, filed Sep. 2, 2009, and is incorporated herein by reference in its entirety.

FIELD

The subject disclosure relates to medical instruments employing luer connectors, and, in particular, to methods and arrangements for disinfecting fluid connectors.

BACKGROUND

Luer connectors as used in medical applications are generally designed to be connected to a patient's IV line, drug or solution source, or other medical implements. For example, in IV dispensing systems, a male luer connector may be connected to a fluid source, and a female needleless luer connector having a needless valve may be connected to a catheter via an infusion line.

It is important to disinfect an exposed surface of a female luer connector before the female connector is mated with a male luer connector. Unless such a disinfection operation is performed on the exposed surface, any microbes (e.g., bacteria) that are present on the surface can find their way into a patient's blood stream via a catheter, thereby exposing the patient to a serious health risk associated with bloodstream infections caused by the microbes.

Typically, the disinfection operation is performed by a nurse or other caregiver who is required to apply a disinfectant swab to the exposed surface prior to the male-to-female luer connection. However, there have been numerous studies that indicate that nurses do not consistently disinfect needleless luer connectors and while education improves compliance, the compliance degrades over time. Causes of the non-compliance include: nurses not having disinfectant swabs at hand and neglecting the duty to obtain more; and the nurses forgetting the requirement to apply disinfectant swabs in the first place. As indicated above, not properly cleaning and disinfecting the connectors can contribute to catheter related blood stream infections and other catheter related complications.

Accordingly, there is a need for a device, system and method that can increase the probability that an exposed surface of a female luer connector receives a disinfectant swab before a male-to-female luer connection is made.

SUMMARY

Embodiments described herein address the foregoing problem by providing a disinfecting male luer connector cap that in one end can be threaded or otherwise coupled to a male luer connector. The male luer connector cap includes a chamber at the opposite end that contains a disinfectant (e.g., isopropyl alcohol or chlorhexidine) impregnating a sponge or other absorptive matrix in the chamber and a sealing member (e.g., a peelable lid) for sealing the disinfectant and the impregnated matrix in the chamber. The chamber is at least partially opened by movement of the sealing member (e.g., removal of a peelable lid) so that an exposed portion of a female luer connector that needs to be disinfected can come in contact with the disinfectant.

Certain embodiments provide a male luer connector cap. The male luer connector cap comprises a connecting portion configured to be coupled to a male luer connector. The male luer connector cap further comprises a body portion having a proximal end coupled to the connecting portion, a distal end opposite to the proximal end, and a chamber formed between the proximal and distal ends, the chamber containing a disinfectant. The male luer connector cap further comprises a sealing member coupled to the body portion at the distal end and configured to prevent leakage of the disinfectant. The chamber is configured to be at least partially opened by movement of the sealing member and to provide an exposed portion of a female luer connector access to the chamber containing the disinfectant.

Certain embodiments provide a male luer connector and cap assembly. The male luer connector and cap assembly comprises a male luer connector having a housing portion, the housing portion having a luer screw thread formed therein. The male luer connector and cap assembly further comprises a male luer connector cap coupled to the male luer connector. The male luer connector cap comprises a connecting portion configured to be coupled to the male luer connector. The male luer connector cap further comprises a body portion having a proximal end coupled to the connecting portion, a distal end opposite to the proximal end, and a chamber formed between the proximal and distal ends, the chamber containing a disinfectant. The male luer connector cap further comprises a sealing member coupled to the body portion at the distal end and configured to prevent leakage of the disinfectant. The chamber is configured to be at least partially opened by movement of the sealing member and to provide an exposed portion of a female luer connector access to the chamber containing the disinfectant.

Certain embodiments provides a method of disinfecting an exposed portion of a female luer connector. The method comprises providing a male luer connector coupled to a male luer connector cap, the male luer connector cap having a chamber containing a disinfectant and a sealing member for sealing the disinfectant in the chamber. The method further comprises at least partially opening the chamber by movement of the sealing member to expose the disinfectant. The method further comprises causing an exposed portion of a female luer connector to come in contact with the disinfecting fluid in the chamber prior to the female luer connector mating with the male luer connector.

It is to be understood that both the foregoing summary and the following detailed description are exemplary and explanatory and are intended to provide further explanation of the embodiments as claimed.

BRIEF DESCRIPTION OF THE DRAWINGS

The accompanying drawings, which are included to provide further understanding of the invention and are incorporated in and constitute a part of this specification, illustrate disclosed embodiments and together with the description serve to explain the principles of the disclosed embodiments.

FIGS. 4A-F are cross-sectional views depicting configurations of the male and female luer connectors and/or the disinfecting male luer connector cap at various stages of the disinfection process of FIG. 3 according to certain aspects of the subject disclosure.

DETAILED DESCRIPTION

In the following detailed description, numerous specific details are set forth to provide a full understanding of the disclosed and claimed embodiments. It will be apparent, however, to one ordinarily skilled in the art that the embodiments may be practiced without some of these specific details. In other instances, well-known structures and techniques have not been shown in detail to avoid unnecessarily obscuring the disclosure.

The word "exemplary" is used herein to mean "serving as an example, instance, or illustration." Any embodiment or design described herein as "exemplary" is not necessarily to be construed as preferred or advantageous over other embodiments or designs.

Figure 1:
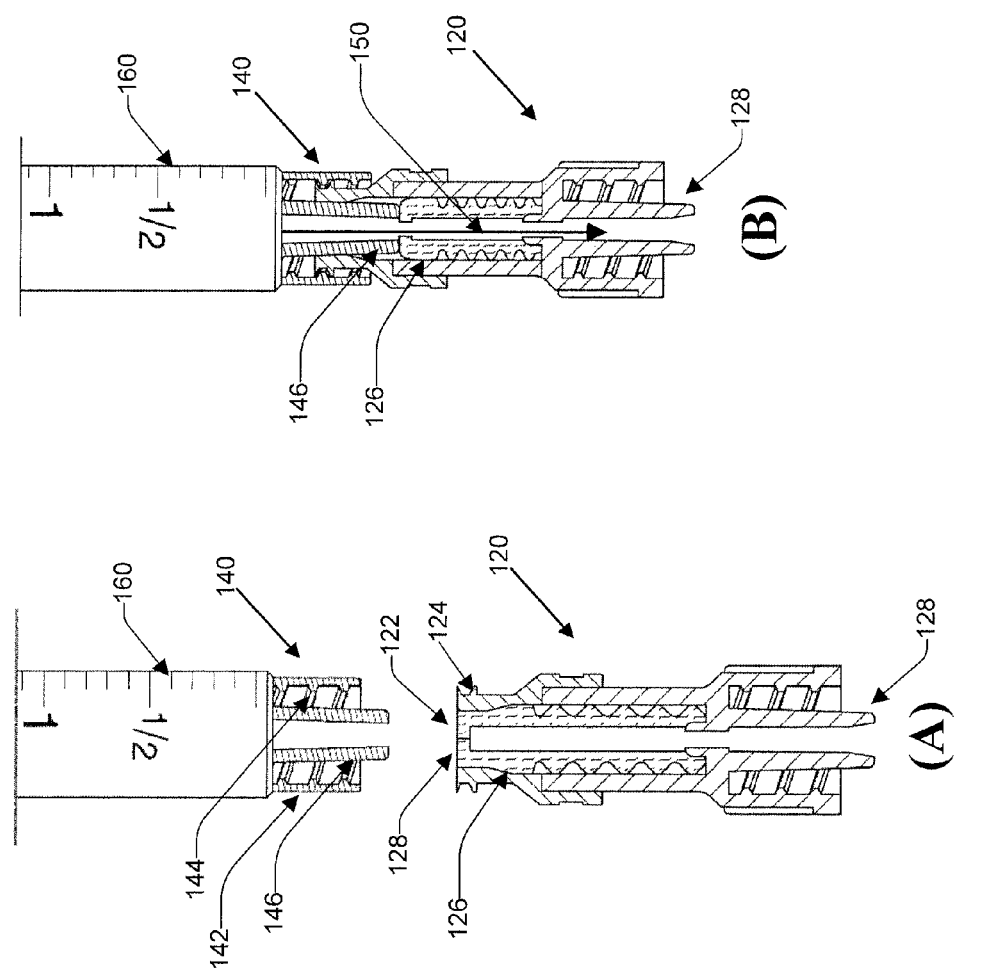
FIGS. 1A and 1B are cross-sectional views depicting a female luer connector and a male luer connector before and after making a needleless liter connection, respectively.

FIGS. 1A and 1B are cross-sectional views depicting a female luer connector 10 and a male luer connector 140 before and after making a needleless luer connection, respectively. Various examples of similar needleless female and male luer connectors are disclosed in U.S. Pat. No. 7,184,825, for example. In the illustrated example, the male luer connector 140 includes a housing 142 having a first luer screw thread 144 formed therein. The male luer connector 140 further includes a male cannula (e.g, a male luer taper) 146. In the illustrated example, the male luer connector 140 is connected to a syringe 160, but in other embodiments, the male luer connector may be connected to a fluid source (e.g., an IV bag) via an IV tubing or other connection.

The female luer connector 120 includes an inlet port 122 and an outlet port 128. The inlet port 122 is sized to receive the male cannula 146 of the male luer connector 140. Disposed within the inlet port 122 is a needleless valve 126 that is configured to provide a fluid path 150 that communicates with the outlet port 128 when the male luer connector 140 is mated with the female luer connector 120. The outlet port 128 of the female luer connector 120 is typically connected to an IV catheter that communicates with a patient's venous system.

As shown in FIGS. 1A and B, the needleless valve 126 has an exposed surface 128 which is engaged by the tip of the male cannula 146 when the male and female luer connectors 120, 140 are mated to each other. As can be seen from FIG. 1B, at least a portion of the exposed surface 128 is exposed to the IV fluid in the fluid path 150. Therefore, any microbes (e.g., bacteria) that are present on the exposed surface 128 can find their way into a patient's blood stream via a catheter, thereby exposing the patient to a serious health risk. However, as indicated above, it may occur that a nurse does not apply a disinfectant swab to the exposed surface 128 prior to the male-to-female luer connection because he/she does not have a disinfectant swab on him/her; or he or she has simply forgotten about the requirement.

Figure 2B:
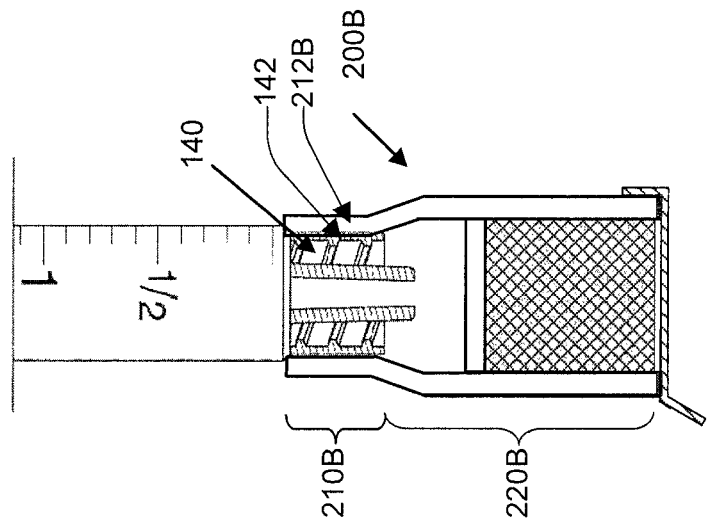
FIGS. 2A-D depict various exemplary disinfecting male luer connector caps according to different aspects of the subject disclosure.
Figure 2A:
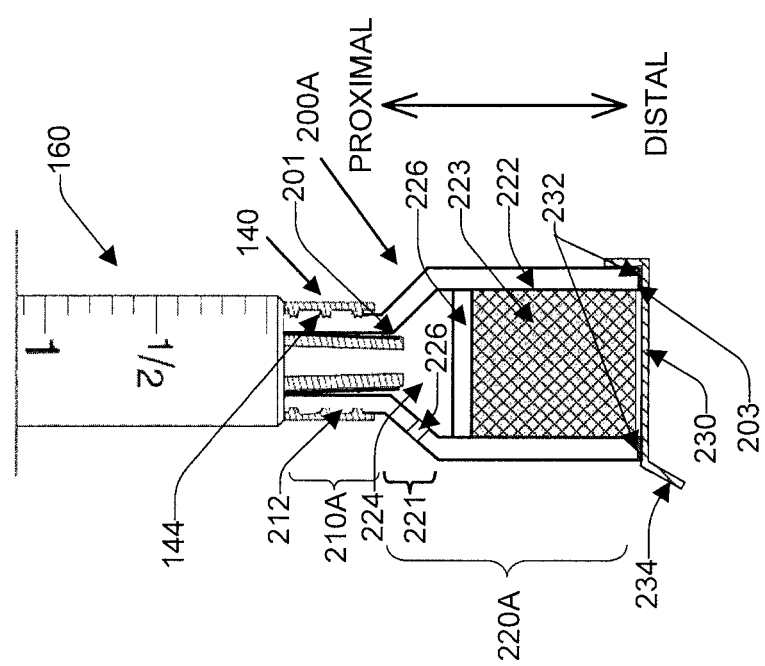

The problem of not applying a disinfectant swab due to the above-identified causes can be alleviated by providing a male luer connector 140 with a disinfecting male luer connector cap 200A as illustrated by FIG. 2A according to certain embodiments. In one aspect, the male luer connector cap 200A acts as a protective cap to prevent the male luer connector 140 from being exposed to contaminants (e.g., dust) and microbes (e.g., bacteria). The male luer connector cap 200A includes a connecting portion 210 configured to be coupled to the male luer connector 140. In the illustrated example of FIG. 2A, the connecting portion 210A includes a threaded portion 212 comprising an external male luer screw thread formed thereon and configured to be threadedly engaged with a counterpart internal female luer screw thread 144 formed on the male luer connector 140.

However, it shall be appreciated by those skilled in the art in view of the subject disclosure that a coupling mechanism other than the threaded coupling mechanism shown in FIG. 2A may be employed without departing from the scope of the subject disclosure. By way of example, FIG. 2B depicts an alternative exemplary disinfecting male luer connector cap 200B that employs a slip-fitting mechanism to provide a coupling between the male luer connector cap 200B and the male luer connector 140. The male luer connector cap 200B includes a connecting portion 210B and a body portion 220B. The connecting portion 210B includes a sleeve 212B configured to be slip fitted over an outside surface of 142 of the male luer connector 140. The sleeve 212B can be made of resilient material such as silicone so as to grippingly engage the outside surface 142. In some embodiments, the entire male luer connector cap 200B maybe formed (e.g., molded, extruded) from such a resilient material.

Returning to FIG. 2A, the disinfecting male luer connector cap 200A further includes a body portion 220A having a proximal end 201 and a distal end 203. The proximal end 201 of the body portion 220 is coupled to the connecting portion 210A and includes a chamber 222 formed between the proximal and distal ends 201, 203. The chamber 222 is separated from the rest of the internal space of the body portion 220A by a partition member 226. In certain embodiments, the body portion 220A is sized (e.g., enlarged from the connecting portion 210A in diameter) such that a portion of a female luer connector that needs to be cleaned/disinfected can enter the chamber 222. In the illustrated example, the enlargement is achieved by introducing a taper in a transition region 221 of the body portion 220A.

The chamber 222 contains a disinfectant fluid that has antimicrobial properties. Examples of such disinfectant fluids include, but are not limited to, asisopropyl alcohol, chlorhexidine gluconate, chlorhexidine diacetate, chlorosylenol, povidone iodine, Triclosan, benzethonium chloride, benzalkonium chloride, octenidine, antibiotics. In certain embodiments, the chamber 222 further includes a matrix 223 that is configured to absorb at least some of the disinfectant fluid to be impregnated therewith. The matrix 223 can be any fluid-absorbing material, non-limiting examples of which include a form sponge made of polyurethane, polyester, cotton, and the like. In certain embodiments, the matrix 223 is at least partially attached (e.g., glued) to an inside surface of the chamber 222 and/or the partition member 226 to prevent movement of the matrix material during a disinfecting/cleaning process to be described below with respect to FIG. 4C.

The disinfecting male luer connector cap 200A further includes a sealing member 230 coupled to the distal end 203 of the body portion 220A and configured to provide a sealing (e.g., leakage prevention) of the disinfectant fluid in the chamber 222. In the illustrated example of FIG. 2A, the sealing member 230 is a peelable lid. In certain embodiments, the sealing is achieved via a sealant material 232 disposed between the peelable lid 230 and the distal end 203 of the body portion 220B. In the illustrated example, the peelable lid 230 includes a tab portion 234 for ease of peeling. The chamber 222 is configured to be at least partially opened by movement of the sealing member 230 (e.g., peeling of the peelable lid), thereby providing an exposed surface of a female luer connector access to the chamber 222 containing the disinfectant.

However, it shall be appreciated by those skilled in the art in view of the subject disclosure that a sealing mechanism other than the peelable lid may be employed without departing from the scope of the subject disclosure. By way of example, FIG. 2C depicts an alternative exemplary disinfecting male luer connector cap 200C that employs a hinged lid 230C to provide the sealing of the disinfectant inside the chamber 222. The male connector cap 200C includes a connecting portion 210C, a body portion 220C and a hinged lid 230C. The hinged lid 230C includes a cover portion 231 that covers a distal end 203C of the body portion 220C. The body portion 220C includes a hinge portion 233C about which the hinged lid 230C is configured to rotatably pivot as illustrated by arrow 205. In the illustrated example, the hinged lid 230C also includes a rib portion 233C that is configured to make a sealing engagement with the inside wall of the chamber 222. Alternatively, the sealing may be achieved via a sealant material disposed between the cover portion 231 and the distal end 203C of the body portion 220C in lieu of or in addition to the sealing provided by the rib portion 233C.

Figure 2D:
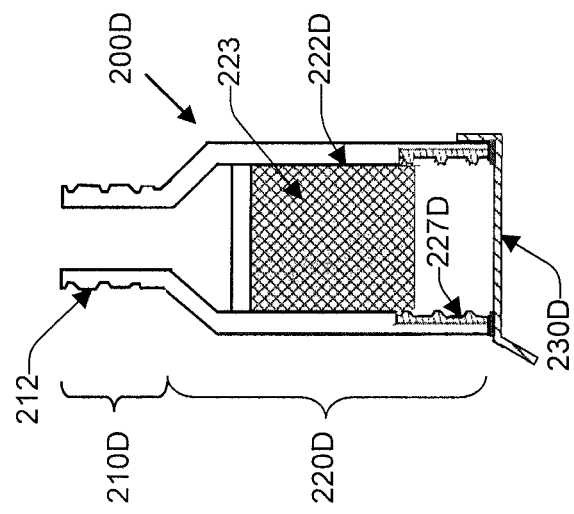
Figure 2C:
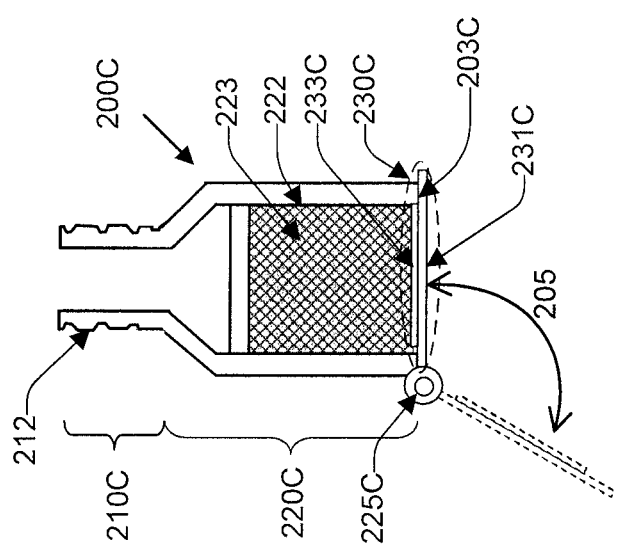

FIG. 2D depicts another alternative exemplary disinfecting male luer connector cap 200D which is configured to make a threaded connection with a female luer connector during a disinfection operation to be described below with respect to FIG. 3. The male luer connector cap 200D includes a connecting portion 210D, a body portion 220D, and a sealing member 230D. In the illustrated embodiment, the body portion 220D of the male luer connector cap 200D includes an internal female luer thread 227D formed therein and configured to make a threaded connection to an exterior male thread 124 of the female luer connector 120 (FIG. 1A) after removal of the sealing member 230D. In the illustrated embodiment, the sealing member 230D is a peelable lid. However, it shall be appreciated that a sealing mechanism other than the peelable lid, such as a hinged lid discussed above or a threaded cap having a male luer thread to be engaged with the internal female luer thread 227D of the body portion 220D, may be used without departing from the scope of the subject disclosure. With this embodiment, a nurse or other caregiver will interconnect the female luer connector 120 to the male luer connector cap 200D to disinfect the female luer connector 120, using the same motion as will be used to connect the female luer connector 120 to the male luer connector 140. Requiring the same motion to make the connection for disinfecting as will eventually be used for establishing a fluid connection allows a nurse or caregiver to perform the customary and usual motions associated with luer connectors.

Returning to FIG. 2A, as the disinfecting male luer connector cap 200A is coupled to the male luer connector 140, a cavity 224 is formed between the male luer connector 140 and the partition member 226. The cavity 224 is in communication with (e.g., fluidically connected to) the male luer connector 140. In certain embodiments, an aperture 226 is provide on the wall of the body portion 220A. The aperture 226 provides an air passage from the cavity 224 to the outside through which air inside an IV fluid delivery system (e.g., the syringe 160) connected to the male luer connector 140 may be purged and the system primed for IV infusion. Such a priming operation via the aperture 226 will be described below with respect to FIG. 3.

Figure 3:
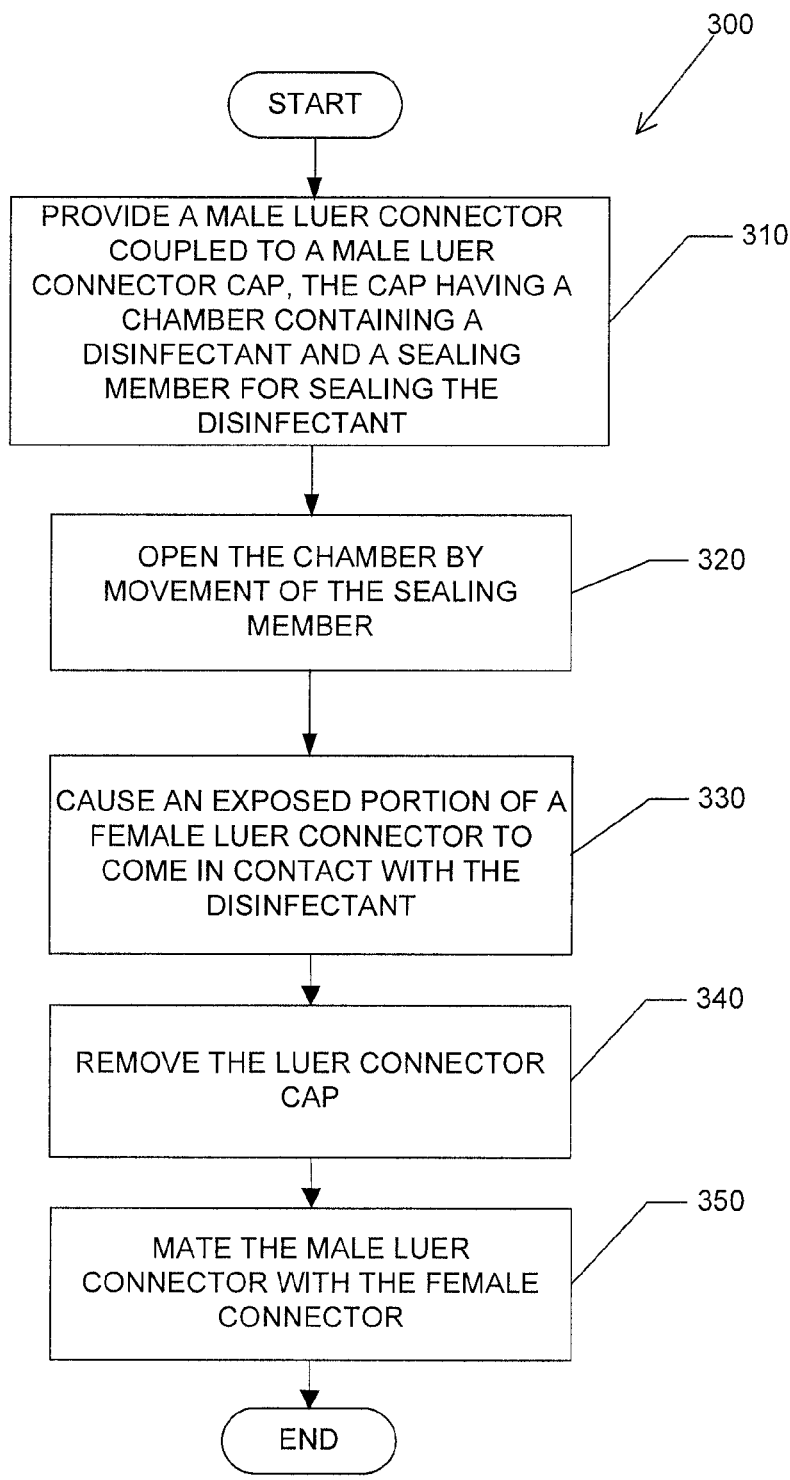
FIG. 3 is a flowchart illustrating an exemplary process 300 for disinfecting an exposed portion of a female luer connector prior to a male-to-female luer connection by the use of a disinfecting male luer connector cap according to certain aspects of the subject disclosure.
Figure 4D:
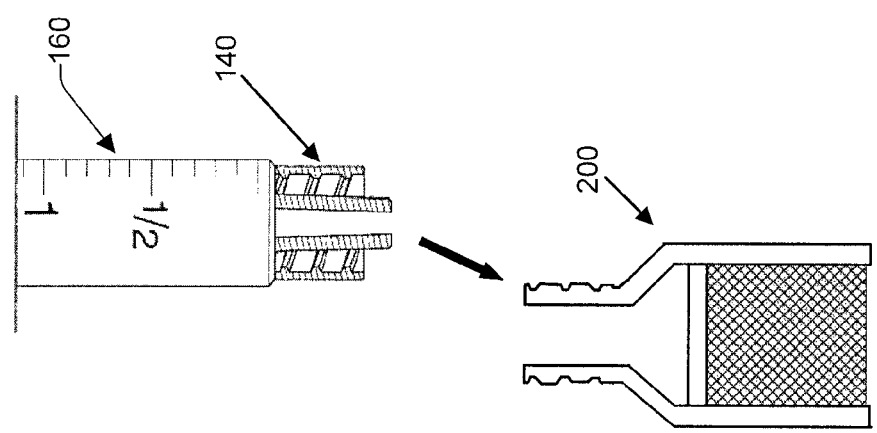

FIG. 3 is a flowchart illustrating an exemplary process 300 for disinfecting an exposed portion of a female luer connector prior to a male-to-female luer connection by the use of a disinfecting male luer connector cap according to certain aspects of the subject disclosure. For the purpose of illustration only, the process 300 will be described with references to FIGS. 4A-D which depict configurations of the male and female luer connectors 120, 140 and/or the disinfecting male luer connector cap 200 at various stages of the process 300. The process 300 begins at a start state and proceeds to operation 310, in which a male luer connector 140 coupled to a disinfecting male luer connector cap 200 is provided as illustrated by FIG. 4A. The male luer connector cap 200 includes a chamber 222 containing a disinfectant and a matrix 223 impregnated with the disinfectant, and a sealing member 230 for sealing the disinfectant inside the chamber 222. In the illustrated embodiment, the male luer connector 140 is coupled to the male luer connector cap 200 via a thread mechanism comprising an internal female luer screw thread 144 formed on the male luer connector 140 and a counterpart external male luer screw thread 212 formed on a connecting portion 210 of the male luer connector cap 200. In other embodiments, the male luer connector 140 may be coupled to the male luer connector cap 200 via a slip fitting mechanism as described above with respect to FIG. 2B.

The process 300 proceeds to operation 320, in which the chamber 222 is opened by movement of the sealing member 230 to expose the disinfectant contained in the chamber as illustrated by FIG. 4B. In the illustrated embodiment in which the sealing member 230 is a peelable lid, the movement involves a nurse or other caregiver holding a tab 234 of the peelable lid 230 and peeling off the lid 230. In other embodiments in which the sealing member 230 is a hinged lid such as the hinged lid 230C shown in FIG. 2C, the movement involves pivoting the hinged lid 230C about the hinge 233C.

The process 300 proceeds to operation 330, in which an exposed portion of a female luer connector 120 to be cleaned/disinfected receives a disinfectant swab by being brought into contact with the disinfectant exposed by the opening of the chamber 222 as illustrated by FIG. 4C. The exposed portion that receives the disinfectant swab includes an exposed surface 128 of a needleless valve 126 disposed inside the female luer connector 120. For example, a nurse or other caregiver may hold a connector-cap assembly comprising the male luer connector 140 and the disinfecting male luer connector cap 200 with fingers and rotate the assembly thereby causing the disinfectant-impregnated matrix to rub against the exposed surface 128 as indicated by a curved arrow in FIG. 4C. By such a rotational movement, the exposed surface 128 is cleaned and disinfected by the disinfectant-impregnated matrix 223. In those embodiments in which the disinfecting male luer connector cap has an internal female luer thread, such as the male luer connector cap 200D shown in FIG. 2D, during the cleaning/disinfecting operation 330, a nurse or other caregiver may threadedly couple the female luer connector 140 to the male luer connector by engaging the external male luer thread 124 of the female luer connector 120 into the internal female luer thread 227D of the male luer connector cap 200D. During the engagement process, the exposed surface 128 of the female luer connector 120 moves in a helical path against the disinfectant-impregnated matrix 223 inside the chamber 222D, whereby the exposed surface 128 is cleaned/disinfected by the matrix 223. In yet other embodiments, a nurse or other caregiver may decouple the disinfecting male luer connector cap 200 from the male luer connector 140 and hold the cap 200 with fingers and apply a disinfecting swab to the exposed surface 128, for example, by rotating either the cap 200 or the female luer connector 120 or both. In yet other embodiments, the exposed surface 128 is dipped into and made to come into contact with the disinfectant inside the chamber 222 without such a rubbing action induced by the rotational movement of the connector-cap assembly. In yet other embodiments, the disinfectant is pressurized inside the chamber 222, and, upon removal of the sealing member 230 or by use of some other activation mechanism (e.g., by push of a button), the pressurized disinfectant is sprayed against the exposed surface 128. Regardless of the contact mechanism, all or some of the microbes that were present on the exposed surface 128 are destroyed or otherwise eliminated from the exposed surface 128 at least in part by the action of the disinfectant that the microbes are made to come in contact with.

As indicated above with respect to FIG. 2A, in certain embodiments, an IV delivery system (e.g., a fluid source and/or an IV tube connecting the fluid source to a male luer connector) is primed by purging air present in the system via an aperture provided in an disinfecting male luer connector (e.g., the aperture 226).

Figure 4E:
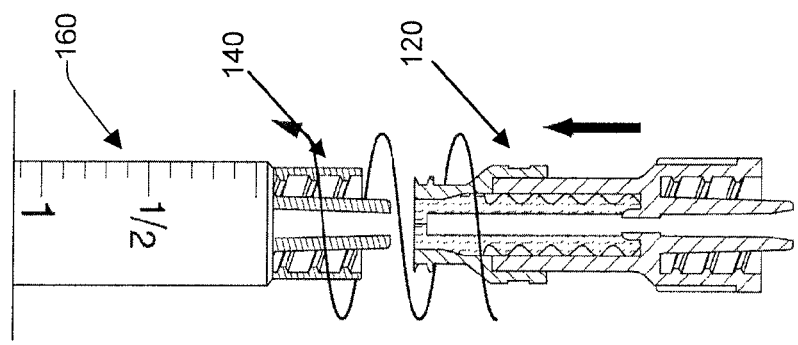
Figure 4F:
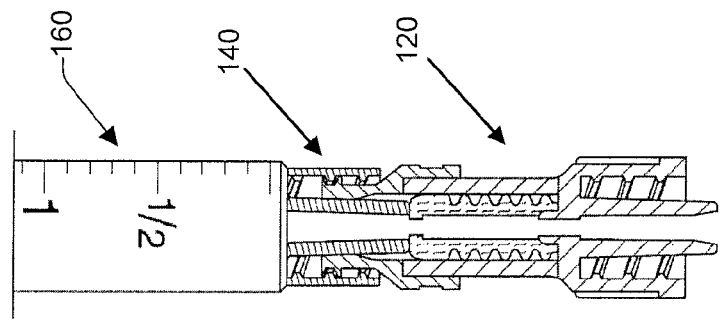

The process 300 proceeds to operation 340, in which, after the cleaning/disinfection operation 330, the male luer connector 200 is decoupled (e.g., unscrewed, slipped oft) from the male luer connector 140 and discarded as illustrated by FIG. 4D. However, as alluded to above, in certain embodiments, the decoupling operation 340 precedes the cleaning/disinfection operation 330. The process 300 then proceeds to operation 350, in which the male luer connector 140, without the male luer connector cap 200, is mated with the disinfected female luer connector 120 as illustrated by FIGS. 4E and 4F.

It shall be appreciated by those skilled in the art that the disinfection device, system, and method described herein provide certain features. For example, the disinfecting male luer connector cap coupled to a male luer connector according to the subject disclosure serves to provide a protective cover for the male luer connector and, at the same time, a disinfectant swab for a nurse to clean/disinfect an exposed surface of a counterpart female luer connector. Furthermore, the presence of the disinfecting male luer connector cap that needs to be decoupled prior to the making of the male-to-female luer connection provides a strong reminder to a nurse that he/she has to apply a disinfectant swab to the female luer connector. Additionally, in certain embodiments the cleaning/disinfecting operation is performed while the disinfecting male luer cap remains coupled to the male luer connector during disinfection of the female luer connector, thereby facilitating the operation through the elimination of the need to separately hold the male luer connector during the female operation or to find a clean surface for the male luer connector during the disinfecting of the female luer connector. However, the disinfecting male luer cap can also be disconnected and be used to disinfect the female luer connector, in other embodiments. The presently disclosed arrangements allow both methods to be performed. Accordingly, the disinfection device, system and method described herein helps to assure that an exposed surface of a female luer connector receives the potentially life-saving disinfectant swab before the male-to-female luer connection is made.

The foregoing description is provided to enable any person skilled in the art to practice the various embodiments described herein. While the foregoing embodiments have been particularly described with reference to the various figures and embodiments, it should be understood that these are for illustration purposes only and should not be taken as limiting.

There may be other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

What is claimed is:

1. A male luer connector cap comprising:
   a connecting portion having a luer screw thread that, in use, threadingly engages a male luer connector, such that a central post of the male luer connector is received within a lumen of the connecting portion;
   a body portion having a proximal end coupled to the connecting portion, a distal end opposite to the proximal end, a chamber formed between the proximal and distal ends, the chamber containing a disinfectant, a cavity in communication with the male luer connector and fluidly isolated from the chamber by a partition wall, and an aperture through a sidewall of the body portion between the luer screw thread and the partition wall that provides an air passage extending from within the cavity to outside the body portion; and
   a sealing member coupled to the body portion at the distal end and configured to prevent leakage of the disinfectant,
   wherein the chamber is configured to be at least partially opened by movement of the sealing member and to provide an exposed portion of a female luer connector access to the chamber containing the disinfectant.

2. The male luer connector cap of claim 1, wherein the female luer connector comprises a needleless valve.

3. The male luer connector cap of claim 1, wherein the chamber is sized to allow entry of the exposed portion of the female luer connector into the chamber from the distal end.

4. The male luer connector cap of claim 1, wherein the disinfectant comprises a disinfectant fluid.

5. The male luer connector cap of claim 4, wherein the chamber further contains a matrix for absorbing at least some of the disinfectant fluid.

6. The male luer connector cap of claim 5, wherein the matrix comprises a foam sponge.

7. The male luer connector cap of claim 5, wherein the matrix is at least partly attached to a surface inside the chamber.

8. The male luer connector cap of claim 1, wherein the body portion comprises a female luer thread formed therein at the distal end, the female luer thread configured to be engaged with a counterpart male thread of the female luer connector.

9. A male luer connector and cap assembly comprising:
   a male luer connector having a housing portion, the housing portion having a luer screw thread formed therein; and
   a male luer connector cap coupled to the male luer connector and comprising:
      a connecting portion having a luer screw thread about an exterior portion that, in use, threadingly engages the male luer connector, such that a central post of the male luer connector is received within a lumen of the connecting portion,
      a body portion having a proximal end coupled to the connecting portion, a distal end opposite to the proximal end, and a chamber formed between the proximal and distal ends, the chamber containing a disinfectant, a cavity in communication with the male luer connector and fluidly isolated from the chamber by a partition wall, and an aperture through a sidewall of the body portion between the luer screw thread and the partition wall that provides an air passage extending from within the cavity to outside the body portion, and a sealing member coupled to the body portion at the distal end and configured to prevent leakage of the disinfectant, wherein the chamber is configured to be at least partially opened by movement of the sealing member and to provide an exposed portion of a female luer connector access to the chamber containing the disinfectant.

10. The male luer connector and cap assembly of claim 9, wherein the male luer connector is coupled to a syringe.

11. The male luer connector and cap assembly of claim 9, wherein the chamber is sized to allow entry of an exposed portion of the female luer connector into the chamber from the distal end.

12. The male luer connector and cap assembly of claim 9, wherein the disinfectant comprises a disinfectant fluid absorbed in a matrix.

13. The male luer connector and cap assembly of claim 9, wherein the male luer valve comprises a needleless valve.

14. The male luer connector and cap assembly of claim 13, wherein the exposed portion comprises an exposed surface of the needleless valve.

15. The male luer connector and cap assembly of claim 9, wherein the body is configured to purge air through the aperture during priming of an IV fluid delivery system connected to the male luer connector.

16. A method of disinfecting an exposed portion of a female luer connector, the method comprising:

providing a male luer connector coupled to a male luer connector cap, the male luer connector cap having (i) a chamber containing a disinfectant, (ii) a sealing member for sealing the disinfectant in the chamber, (iii) a connecting portion having a luer screw thread about an exterior portion that, in use, threadingly engages the male luer connector, such that a central post of the male luer connector is received within a lumen of the connecting portion, and (iv) a cavity in communication with the male luer connector and fluidly isolated from the chamber by a partition wall;

purging air from within the cavity through an aperture in a sidewall of the body portion between the luer screw thread and the partition wall;

at least partially opening the chamber by movement of the sealing member to expose the disinfectant; and causing an exposed portion of a female luer connector to come in contact with the disinfecting fluid in the chamber prior to the female luer connector mating with the male luer connector.

17. The method of claim 16, wherein the female luer connector comprises a needleless valve.

18. The method of claim 17, wherein the causing comprises applying a disinfectant swab containing the disinfecting fluid to an exposed surface of the needleless valve.

19. The method of claim 16, wherein the causing comprises threadedly engaging the female luer connector to the male luer connector cap.

20. The method of claim 16 further comprising decoupling the male luer connector cap from the male luer connector prior to the female luer connector mating with the male luer connector.

21. The method of claim 20 further comprising priming an IV delivery system attached to the male luer connector prior to the decoupling.

22. The method of claim 21, wherein the priming comprises purging air present in the IV delivery system via the aperture.

* * * * *